United States Patent [19]

Ritterband et al.

[11] Patent Number: 5,698,395
[45] Date of Patent: Dec. 16, 1997

[54] APPARATUS FOR SEPARATION, CONCENTRATION AND DETECTION OF TARGET MOLECULES IN A LIQUID SAMPLE

[76] Inventors: Menachem Ritterband, 9B Maccabi Street, Ness Ziona 70400; Sara Alajem, 64, Kfar Hanagid, 76875; Michal Schrift, 6 Hapalmach Street, Kiryat Gat 82000; Ileana Rusu, 70/3 Derech Yavne, Rehovot 76341; Avraham Reinhartz, 1 Israel Shahar Street, Rehovot 76450, all of Israel

[21] Appl. No.: 297,805

[22] Filed: Aug. 30, 1994

[30] Foreign Application Priority Data

Dec. 23, 1993 [IL] Israel .................................. 108159

[51] Int. Cl.[6] .................. C12Q 1/68; G01N 33/543; G01N 33/548; G01N 33/552
[52] U.S. Cl. .................. 435/6; 422/56; 422/57; 422/58; 422/61; 422/68.1; 435/7.1; 435/287.1; 435/287.2; 435/287.7; 435/287.8; 435/805; 435/810; 436/514; 436/518; 436/524; 436/527; 436/528; 436/530; 436/805
[58] Field of Search .................. 422/56, 57, 61, 422/68.1; 435/4, 6, 7.1, 7.9, 7.92, 805, 969, 970, 287.1, 287.2, 287.7, 287.8, 810; 436/518, 524, 528, 906, 514, 530, 805, 527

[56] References Cited

U.S. PATENT DOCUMENTS

| | | |
|---|---|---|
| 4,522,923 | 6/1985 | Deutsch et al. .................. 422/57 |
| 4,857,453 | 8/1989 | Ullman .................. 422/58 |
| 5,114,673 | 5/1992 | Berger et al. .................. 422/56 |
| 5,232,663 | 8/1993 | Wilk et al. .................. 422/56 |
| 5,244,631 | 9/1993 | Morikawa .................. 422/56 |

FOREIGN PATENT DOCUMENTS

| | | |
|---|---|---|
| 0262328 | 7/1987 | European Pat. Off. . |
| 9115769 | 10/1991 | WIPO . |

*Primary Examiner*—Paula K. Hutzell
*Assistant Examiner*—James L. Grun

[57] ABSTRACT

This disclosure describes an apparatus for separation and detection of target molecules in a liquid sample containing the target molecules and non-target molecules comprising at least one absorption area, a bibulous carrier defining a first liquid transport path in fluid contact with at least one absorption area including at least one reaction area upstream of the at least one absorption area wherein the reaction area includes a capture reagent and a sample area upstream of the reaction area wherein the liquid sample when applied to sample area is transported by capillary action past the reaction area where at least a portion of the target molecules may be bound to the capture reagent to permit detection of the target molecules. The liquid sample is then transported by capillary action on to the absorption area. A second liquid transport path is in fluid communication with the reaction area of the bibulous carrier for transporting a washing solution applied to the reaction area to the at least one absorption area thereby removing interfering substances from the reaction area. Means are also provided for alternatively selecting between the first and second liquid transport path during capillary transport of the liquid sample.

22 Claims, 2 Drawing Sheets

5,698,395

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 25
( B ) TYPE: Nucleotide
( C ) STRANDEDNESS: Double
( D ) TOPOLOGY: Circular ( v i ) ORIGINAL SOURCE:
( A ) ORGANISM: Human Papillomavirus ( x i ) SEQUENCE DESCRIPTION: SEQ ID NO:1:

GTTTCAGGAC CCACAGGAGC GACCC                                                      2 5

APPARATUS FOR SEPARATION, CONCENTRATION AND DETECTION OF TARGET MOLECULES IN A LIQUID SAMPLE

FIELD OF THE INVENTION

The invention relates to apparatus for separation concentration and detection of target molecules in a liquid sample.

BACKGROUND OF THE INVENTION

The use of test devices including chromotography as a separation, concentration and detection procedure is well known in the art. For example, European Patent Application 0 262 328 A3 describes a test strip for the detection of analytes such as antigens and antibodies. Chromatographic test devices, such as the device described in U.S. Pat. No. 4,857,453 to Ullman et al, may also be enclosed in a housing.

One limitation of chromotography devices such as those described above is that washing procedures are slow since the washing fluid must pass through the entire length of the chromatographic path. A device in which a washing solution is carried only over a portion of the chromatographic path is described in PCT Application WO 91/15769.

SUMMARY OF THE INVENTION

The present invention provides an improved apparatus for separation, concentration and detection of target molecules in a liquid sample.

There is thus provided apparatus for separation, concentration and detection of target molecules in a liquid sample containing the target molecules and non-target molecules comprising, at least one absorption area, a bibulous carrier defining a first liquid transport path in fluid contact with the at least one absorption area including, at least one reaction area upstream of the at least one absorption area wherein the reaction area includes a capture reagent, and a sample area upstream of the reaction area wherein the liquid sample when applied to sample area is transported by capillary action past the reaction area where at least a portion of the target molecules may be bound to the capture reagent to permit detection of the target molecules and the liquid sample is then transported by capillary action on to the absorption area, a second liquid transport path in fluid communication with the reaction area of the bibulous carrier for transporting a washing solution applied to the reaction area to the at least one absorption thereby removing interfering substances from the reaction area, and apparatus for alternatively selecting between the first and second liquid transport path during capillary transport of the liquid sample.

In accordance with a preferred embodiment of the present invention the apparatus for separation concentration and detection is enclosed in a housing.

In accordance with a another preferred embodiment of the present invention the housing includes a sample port in fluid communication with the sample area.

In accordance with yet another preferred embodiment of the present invention the housing includes a washing port in fluid communication with the reaction area.

In accordance with still another preferred embodiment of the present invention the at least one absorption area includes a first absorption area and a second absorption area.

In accordance with yet another preferred embodiment of the present invention the second absorption area is in direct fluid connection with the first absorption area for prevention of a backflow from the first absorption area through bibulous carrier to the second absorption area.

In accordance with a further preferred embodiment of the present invention the bibulous carrier is a nitrocellulose membrane wherein the absorption sites have been blocked to facilitate transport of the target molecules.

In accordance with a still further preferred embodiment of the present invention the bibulous carrier is a glass fiber matrix.

In accordance with another preferred embodiment of the present invention the apparatus for alternatively selecting includes a fluid impermeable disintegratable partition between the bibulous carrier and the second absorption area.

In accordance with yet another preferred embodiment of the present invention the disintegratable partition is disintegrated by the liquid sample.

In accordance with still another preferred embodiment of the present invention the disintegratable partition is disintegrated by a substance added to the liquid sample.

In accordance with yet another preferred embodiment of the present invention the disintegratable partition is disintegrated by a solution applied to the sample area after the liquid sample is applied.

In accordance with a further preferred embodiment of the present invention the disintegratable partition is disintegrated by a substance applied to the reaction area after binding of the target molecules to the reaction area.

In accordance with a still further preferred embodiment of the present invention the disintegratable partition is disintegrated over a predetermined period of time.

In accordance with yet a further preferred embodiment of the present invention the disintegratable partition is fabricated from a netting embedded in a compound selected from the group including water soluble polymers, pH degradable substances, ionic strength degradable substances and enzymatically digestible substances.

In accordance with another preferred embodiment of the present invention the water soluble polymers include water soluble polyesters.

In accordance with yet another preferred embodiment of the present invention the target molecules include target nucleic acid sequences.

In accordance with still another preferred embodiment of the present invention the target nucleic acid sequences include DNA sequences.

In accordance with yet another preferred embodiment of the present invention the target nucleic acid sequences include RNA sequences.

In accordance with a further preferred embodiment of the present invention the target molecules include antigens.

In accordance with still a further preferred embodiment of the present invention the target molecules include antibodies.

In accordance with yet a further preferred embodiment of the present invention the capture reagent comprises at least one nucleic acid capture reagent including nucleic acid probe sequences complementary to at least part of the target nucleic acid sequences.

In accordance with another preferred embodiment of the present invention the capture reagent comprises at least one antigen.

In accordance with yet another preferred embodiment of the present invention the capture reagent comprises at least one antibody.

BRIEF DESCRIPTION OF THE DRAWINGS

The present invention will be understood and appreciated more fully from the following detailed description taken in conjunction with the drawings in which.

DETAILED DESCRIPTION OF THE PREFERRED EMBODIMENTS

Figure 1:
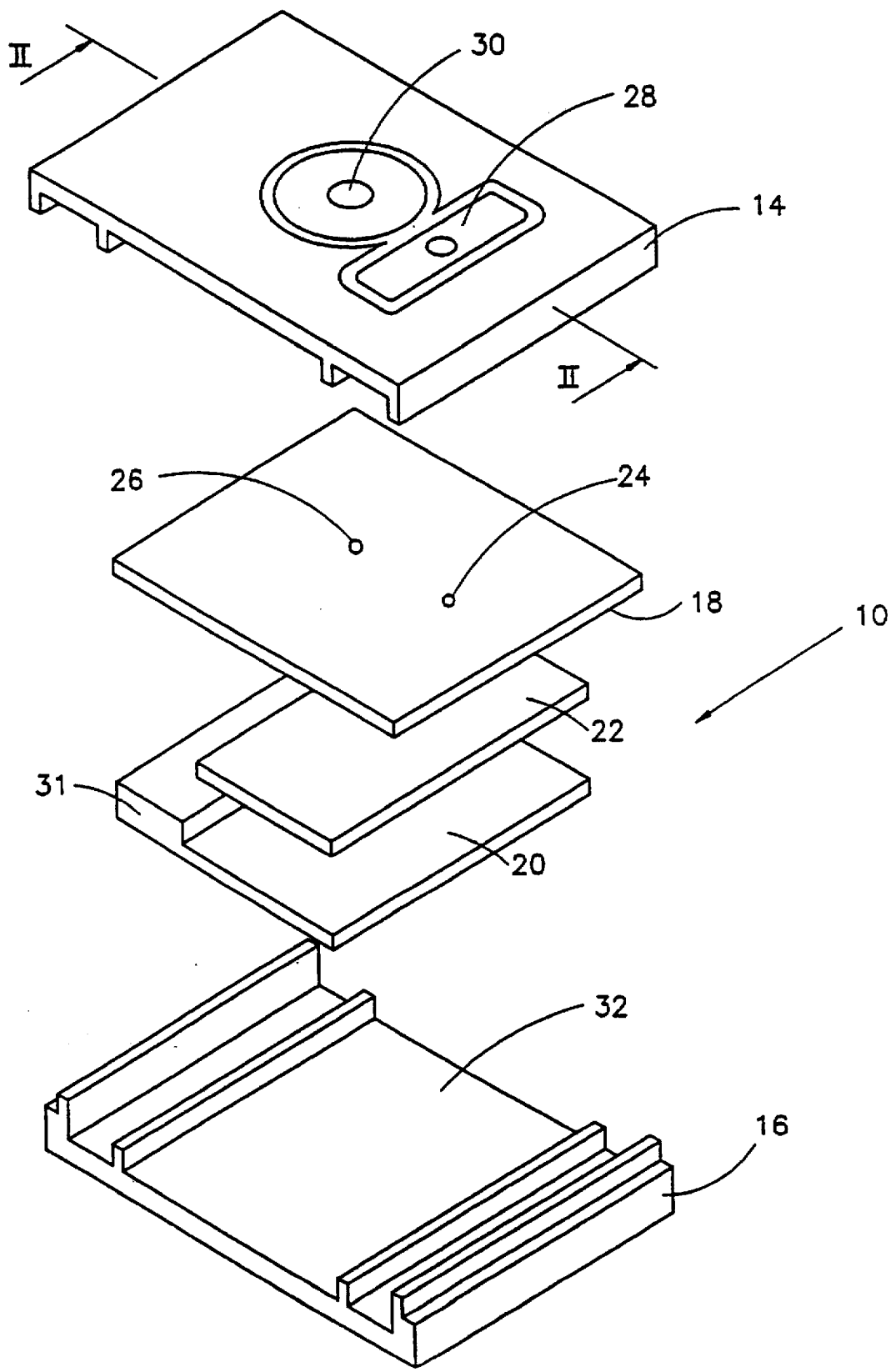
FIG. 1 is an exploded pictorial illustration of apparatus for separation, concentration and detection of target molecules in a liquid sample constructed and operative in accordance with the present invention.
Figure 2:
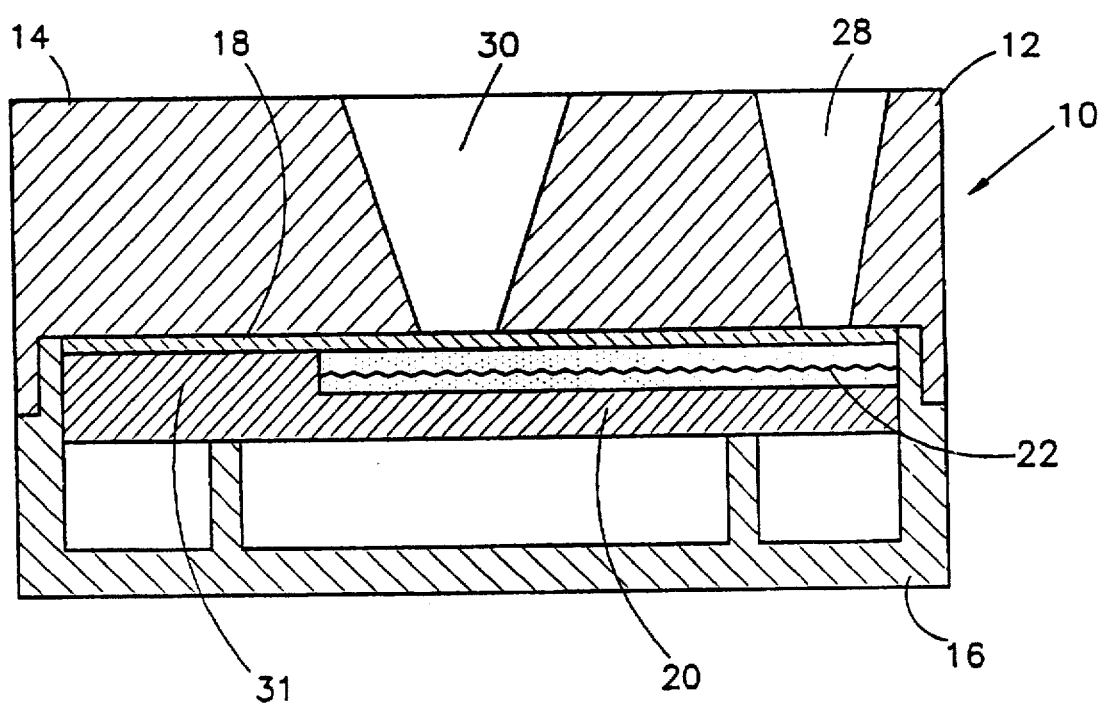
FIG. 2 is a side sectional illustration of the apparatus taken along the line II—II of FIG. 1.

Reference is now made to FIGS. 1 and 2 which illustrate apparatus 10 for separation, concentration and detection of target molecules in a liquid sample constructed and operative in accordance with a preferred embodiment of the present invention.

Apparatus 10 includes a housing 12 fabricated from an injection moldable, radiation sterilizable plastic such as polyethylene. The housing 12 includes a top member 14, and a bottom member 16 which are joined together by any convenient means such as gluing.

The housing typically encloses a bibulous matrix 18, an absorption area 20 and a disintegratable barrier 22. The bibulous matrix 18 when wet forms a capillary transport path in fluid communication with the absorption area and includes a sample area 24 upstream of a reaction area 26 which is in fluid communication with the absorption area 20.

Typically, a liquid sample of 0.1 ml to 1.0 ml in volume including target and non-target molecules is applied to the sample area 24 through a sample port 28 in the top member 14 of the housing 12. The liquid sample is then carried along a first transport path in the bibulous matrix 18 by capillary action from the sample area 24 to the reaction area 26 where the target molecules may be captured by a capture reagent for later detection.

The capture reagent is typically an antibody to the target molecule or a DNA or RNA sequence complementary to at least a portion of the target molecule. Detection is typically accomplished by a colorimetric reaction in the reaction area 26 between a detection reagent and the captured target molecules.

From the reaction area 26 the liquid sample is typically carried along the first transport path to the absorption area 20 by capillary action. A portion 31 of the absorption area 20 typically abuts a lower surface of the bibulous matrix 18 downstream of the reaction area 26 to maximize capillary flow forces in the bibulous matrix 18.

The bibulous matrix 18 and the absorption area 20 are typically fixed to the top member 14 by a pressure sensitive, low soak in adhesive such as depositable adhesive, I.D. No. 62-9985-4830-4, 3M Industrial Specialties Div., St. Paul Minn., USA.

The disintegratable barrier 22 is typically disposed between the first flow path and the absorption area 20 upstream of portion 31. The disintegratable barrier 22 typically abuts and separates the absorption area 20 from the bibulous matrix 18 from a point downstream of the sample port 28 to part of the absorption area 20 downstream of reaction area 26 and upstream of portion 31 of the absorption area 20. The disintegratable barrier 22 typically extends laterally beyond the bibulous matrix 18 and the absorption area 20 and is typically fixed to the top member 14 by a pressure sensitive, low soak in adhesive in the areas not covered by the bibulous matrix 18 or the absorption area 20. The lateral extension of the disintegratable barrier 22 beyond the absorption area 20 blocks direct fluid contact between the bibulous matrix 18 and the absorption area 20 except at portion 31, until the disintegratable barrier 22 is disintegrated.

When the disintegratable barrier 22 is disintegrated a second transport path is established for capillary transport between the reaction area 26 and the absorption area 20 through the bibulous matrix 18. This second transport path can be employed to wash interfering compounds from the reaction area 26 by applying a washing solution to the reaction area 26 through wash port 30 in top member 14.

The disintegratable barrier 22 may be typically fabricated from compounds embedded on a netting platform of plastic polymeric material. These compounds typically include watersoluble polymers such as the polyesters lactic acid and glycolic acid copolymers, pH and/or ionic strength degradable substances such as poly-hydroxymethylacrylate and carbopol and enzymatically digestible substrates such as gelatin which may be digested by gelatinase.

The absorption area 20 is typically fitted into a well 32 in bottom member 16. The absorption area 20 is typically fabricated to absorb all of the liquid to be added to apparatus 10 during use in an assay procedure.

The procedure used for the separation, concentration and detection of target molecules using apparatus 10 typically includes applying 0.05 ml to 0.5 ml of a sample fluid to the sample area 24 of the bibulous matrix 18 through sample port 28. A wash fluid may subsequently be applied to the sample area 24 when the sample fluid volume is insufficient for efficient capillary transport of the sample liquid to the reaction area 26. Either the sample fluid or the wash fluid may contain a compound which disintegrates the disintegratable barrier 22.

Capillary and chromatographic forces within the bibulous matrix 18 draw the fluid portion of the sample along the first transport path from the sample area 24 toward the reaction area 26 and on to the absorption area 20. As the fluid migrates through the reaction area 26, target molecules in the sample fluid react and bind with a specific complementary capture reagent such as an immuno-reagent, a chemical test or a nucleic acid sequence reagents, which has been immobilized to the reaction area 26.

The absorptive capacity of portion 31 and contact between the absorption area 20 and the bibulous matrix 18 at portion 31 prevents a counter flow of fluid along the first transport path from the absorption area 20 back to the reaction area 26 if the bibulous matrix 18 is overloaded. Thus any excess fluid applied to the bibulous matrix 18 or the absorption area 20 will flow into the portion 31 rather than counter flow.

As the fluids are transported in the bibulous matrix 18 along the first transport path, the disintegrative compound contained in either the sample or wash fluid start to cleave the disintegratable barrier 22 which separates the bibulous matrix 18 and the absorption area 20. The time elapsed from the application of the disintegrative compound to disintegration of the disintegratable barrier 22 may typically range from 0.5 to 45 minutes depending on the composition of the disintegratable barrier.

After capillary transport of the fluids applied to the sample area 24 is completed a suitable volume of wash fluid, typically 0.1 ml to 1.5 ml, may be applied directly to the reaction area 26 through the reaction port 30. Typically, the wash fluid applied to the reaction area 26 completes the cleavage of the disintegratable barrier 22 thereby establishing the second transport path through the bibulous matrix 18 between the reaction area 26 and the absorption area 20. This second flow path permits the rapid and efficient washing of the reaction area 26 to remove any unreacted sample molecules or other compounds which may interfere with subsequent steps. The wash fluid applied directly to the reaction area 26 may, however, alternatively contain the disintegrative compound.

After washing of the reaction area 26 an immuno-reagent, or chemical test reagent complementary to the target molecules conjugated with an enzyme or other suitable tracer, is applied directly to the reaction area 26 through reaction port 30. Most of the unbound immuno-reagent conjugate or chemical test reagent is then washed out of the reaction area 26 into the absorption area 20 along the second flow path by application of a washing fluid to the reaction area 26. If the tracer is an enzyme requiring a substrate to develop color, a volume of this substrate or chromogen is applied to the reaction area 26 through reaction port 30 immediately after washing of unbound reagent.

Reference is now made to the following examples which, together with FIGS. 1 and 2 illustrate the invention.

EXAMPLE 1

DETECTION OF HIV

Synthetic HIV-1 (gp-41, gp-120) antigen peptides were immobilized on the reaction zone of a glass fiber matrix. Approximately 300 microliters of pre-diluted blood serum was applied to the sample port 28 of apparatus 10. This was followed by application to the sample port 28 of 150 microliters of a wash solution consisting of 1% gelatin and 0.3% tween-20 in a phosphate buffered saline.

Immediately after the transport of fluids to the reaction area 26 as indicated by the wetting of the reaction area 26 and the disappearance of liquid from the sample area 24, 300 microliters of an affinity purified rabbit anti-human IgG, conjugated to alkaline phosphatase, diluted in a conjugate solution of greater viscosity comprising a phosphate buffered saline solution including 1% gelatin, 1% fetal calf serum, 0.05% tween 20, 1% PVP 700,000 and 0.5% thimerosal, was directly applied to the wetted reaction zone. Unreacted enzyme conjugate was washed out of the reaction area 26 by applying 500 microliters of wash solution to the reaction area 26. Finally, 100 microliters of a substrate chromogen BCIP/NBT was applied to the reaction area 26. Appearance of a colored product at the reaction zone provided evidence of enzyme activity indicative of antibody to HIV-1 present in the sample.

EXAMPLE 2

DETECTION OF HIV-1

Recombinant HIV-1 (gp-41) antigen was immobilized on the reaction zone of a glass fiber matrix. After immobilization of the antigen, the reaction zone was blocked by adding 150 ml of matrix blocker comprising a phosphate buffered saline solution including 1% gelatin, 1% fetal calf serum, 0.05% tween 20, 1% PVP 700,000 and 0.05% thimerosal, to the reaction zone area. The matrix blocker migrated by capillary forces and wetted almost the whole glass fiber matrix.

Approximately 300 microliters of pre-diluted blood serum was applied to the sample port 28 of apparatus 10. This was followed by application to the sample port 28 of 150 microliters of a wash solution consisting of 1% gelatin, 0.05% thimerosal and 0.3% tween-20 in a phosphate buffered saline.

After the transport of fluids to the reaction area 26 as indicated by the wetting of the reaction area 24 and the disappearance of liquid from the sample area 26, 300 microliters of an affinity purified rabbit anti-human IgG, conjugated to alkaline phosphatase, diluted in a conjugate solution of greater viscosity comprising a phosphate buffered saline solution including 1% gelatin, 1% fetal calf serum, 0.05% tween 20, 1% PVP 700,000 and 0.5% thimerosal, was directly applied to the wetted reaction zone. Unreacted enzyme conjugate was washed out of the reaction area 26 by applying 600 microliters of wash solution to the reaction area 26. Finally, 300 microliters of a substrate chromogen BCIP/NBT was applied to the reaction area 26. Appearance of a colored product at the reaction zone provided evidence of enzyme activity indicative of antibody to HIV-1 present in the sample.

EXAMPLE 3

DETECTION OF HIV-1 IN SALIVA

Synthetic HIV-1 (gp-41, gp-120) antigen peptides was immobilized on the reaction zone of a glass fiber matrix. After immobilization of the antigen, the reaction zone was blocked by adding 150 ul of matrix blocker comprising a phosphate buffered saline solution including 1% gelatin, 1% fetal calf serum, 0.05% tween 20, 1% PVP 700,000 and 0.5% thimerosal, to the reaction zone area. The matrix blocker migrated by capillary forces and wetted almost the whole glass fiber matrix.

Approximately 200 microliters of pre-treated saliva was then applied to the sample area 24 of apparatus 10. The saliva was pretreated according to the user manual of Omni-Sal™, Saliva Diagnostic Systems Inc., Trantdale, Oreg., USA.

Immediately after the transport of fluids to the reaction area 26 as indicated by the wetting of the reaction area 26 and the disappearance of liquid from the sample area 24, approximately 200 microliters of an affinity purified rabbit anti-human IgG, conjugated to Carbon Sol particles, Holland Biotechnology Co., Leiden, the Netherlands, diluted in a conjugate solution of greater viscosity comprising a phosphate buffered saline solution including 1% gelatin, 1% fetal calf serum, 0.05% tween 20, 1% PVP 700,000 and 0.5% thimerosal, was directly applied to the wetted reaction zone. Unreacted conjugate was washed out of the reaction area 26 by three applications of 500 microliters of wash solution to the reaction area 26. Appearance of a colored spot at the reaction zone provided evidence indicative of antibody to HIV-1 present in the sample.

EXAMPLE 4

DETECTION OF HELICOBACTER PYLORI

Helicobacter Pylori antigen was immobilized on the reaction zone of a glass fiber matrix. After immobilization of the antigen, the reaction zone was blocked by adding 150 ul of matrix blocker comprising a phosphate buffered saline solution including 1% gelatin, 1% fetal calf serum, 0.05% tween 20, 1% PVP 700,000 and 0.5% thimerosal, to the reaction zone area. The matrix blocker migrated by capillary forces and wetted almost the whole glass fiber matrix.

Approximately 300 microliters of blood serum prediluted in a running solution of 1% gelatin, 0.05% thimerosal and 0.3% tween-20 in a phosphate buffered saline was applied to the sample area 24 of apparatus 10.

Immediately after the transport of fluids to the reaction area 26 as indicated by the wetting of the reaction area 26 and the disappearance of liquid from the sample area 24, 300 microliters of an affinity purified rabbit anti-human IgG, conjugated to alkaline phosphatase, diluted in a conjugate solution of greater viscosity comprising a phosphate buffered saline solution including 1% gelatin, 1% fetal calf serum, 0.05% tween 20, 1% PVP 700,000 and 0.5% thimerosal, was directly applied to the wetted reaction zone. Unreacted enzyme conjugate was washed out of the reaction area 26 by applying 600 microliters of wash solution to the reaction area 26. Finally, 300 microliters of a substrate chromogen BCIP/NBT was applied to the reaction area 24. Appearance of a colored product at the reaction zone provided evidence of enzyme activity indicative of antibody to Helicobacter Pylori present in the sample.

EXAMPLE 5

DETECTION OF HCV

NS-4a-peptide, NS-3 recombinant protein and the core structural peptide of the HCV antigen were immobilized on the reaction zone of a glass fiber matrix. After immobilization of the antigen, the reaction zone was blocked by adding 150 ul of matrix blocker comprising a phosphate buffered saline solution including 1% gelatin, 1% fetal calf serum, 0.05% tween 20, 1% PVP 700,000 and 0.5% thimerosal, to the reaction zone area. The matrix blocker migrated by capillary forces and wetted almost the whole glass fiber matrix.

Approximately 300 microliters of blood serum prediluted in a running solution of 1% gelatin, 0.05% thimerosal and 0.3% tween-20 in a phosphate buffered saline was applied to the sample area 24 of apparatus 10.

Immediately after the transport of fluids to the reaction area 26 as indicated by the wetting of the reaction area 26 and the disappearance of liquid from the sample area 24, 300 microliters of an affinity purified rabbit anti-human IgG, conjugated to alkaline phosphatase, diluted in a conjugate solution of greater viscosity comprising a phosphate buffered saline solution including 1% gelatin, 1% fetal calf serum, 0.05% tween 20, 1% PVP 700,000 and 0.5% thimerosal, was directly applied to the wetted reaction zone. Unreacted enzyme conjugate was washed out of the reaction area 26 by applying 600 microliters of wash solution to the reaction area 26. Finally, 300 microliters of a substrate chromogen BCIP/NBT was applied to the reaction area 26. Appearance of a colored product at the reaction zone provided evidence of enzyme activity indicative of antibody to HCV present in the sample.

EXAMPLE 6

DETECTION OF $HB_S$ ANTIGEN

A mixture of two different monoclonal anti $HB_S$ antibodies in a phosphate buffered saline solution including 0.005% bovine serum albumin and 2% trehalose were immobilized on the reaction zone of a glass fiber matrix. After immobilization of the antigen, the reaction zone was blocked by adding 150 ul of matrix blocker comprising a phosphate buffered saline solution including 2% bovine serum and 1% PVP 700,000, to the sample area 24. The matrix blocker migrated by capillary forces and wetted almost the whole glass fiber matrix.

Approximately 200 microliters of blood serum prediluted in a phosphate buffered saline reaction solution of greater viscosity consisting of 35% serum sample, 0.5% PVP 700000, 1.0% fetal calf serum, 0.002% horse serum, 4.0% dextran sulfate, 0.04% tween 20 and precalibrated volumes of biotinylated monoclonal anti $HB_S$ antibodies and strepavadin APL conjugate was then directly applied to the sample area 24 of apparatus 10.

Immediately after the transport of fluids to the reaction area 26 as indicated by the wetting of the reaction area 26 and the disappearance of liquid from the sample area 24 unreacted enzyme conjugate was washed out of the reaction area 26 by four applications of 500 microliters of wash solution to the reaction area 26. Finally, 200 microliters of a substrate chromogen BCIP/NBT was applied to the reaction area 26. Appearance of a colored product at the reaction zone provided evidence of enzyme activity indicative of $HB_S$ antigen present in the sample.

EXAMPLE 7

DETECTION OF HPV BY HYBRIDIZATION

HPV specific oligonucleotides (GTTTCAGGACCCAC-AGGAGCGACCC (SEQ ID NO:1)) were immobilized on the reaction zone of a glass fiber matrix. DNA from Caski cells was extracted and labeled through sulfonation according to the protocol of Hybricomb™, Orgenics Ltd., Yavne, Israel. The labeled DNA was then diluted 1:10 in a hybridization solution composed of 0.6M NaCl, 20 mM phosphate buffer, pH 7.5, 0.02% Ficoll, 0.02% gelatin, 0.1% tween 20 and 20.0% glycerol.

The sample was then boiled for 20 minutes and then immediately chilled on ice. 200 ul of the solution was applied to the sample area 24 of apparatus 10. After the transport of all the hybridization solution, 100 ul of an affinity purified mouse anti sulfonated DNA conjugated to alkaline-phosphatase diluted in a phosphate buffered saline solution including 1% gelatin and 0.1% tween was then applied to the reaction area 26.

Unreacted enzyme conjugate was washed out of the reaction area 26 by applying 500 microliters of a phosphate buffered saline wash solution including 0.5% tween to the reaction area 26. Finally, 100 microliters of a substrate chromogen BCIP/NBT was applied to the reaction area 26. Appearance of a colored product at the reaction zone provided evidence of enzyme activity indicative specific HPV-16 sequences present in the sample.

It will be appreciated by persons skilled in the art that the present invention is not limited to what has been particularly shown and described herein above. Rather the scope of the present invention is defined only by the claims which follow.

---

We claim:

1. Apparatus for separation, concentration and detection of target molecules in a liquid sample containing the target molecules and non-target molecules comprising:

an absorption member having at least first and second absorption areas;

a bibulous carrier defining a first liquid transport path in fluid contact with said first absorption area, said bibulous carrier comprising:

at least one reaction area upstream of the absorption area and comprising an immobilized capture reagent; and a sample area upstream of the reaction area; and a disintegratable barrier disposed between said bibulous carrier and said second absorption area and being operative, when disintegrated, to provide a second transport path between said bibulous carrier and said absorption member.

2. Apparatus according to claim 1 and also comprising a housing enclosing said absorption member carrier and barrier.

3. Apparatus according to claim 2 wherein the housing comprises a sample port in fluid communication with the sample area.

4. Apparatus according to claim 2 wherein the housing comprises a washing port in fluid communication with the reaction area.

5. Apparatus according to claim 1 wherein the second absorption area is in direct fluid connection with the first absorption area for prevention of a backflow from the first absorption area through bibulous carrier to the second absorption area.

6. Apparatus according to claim 1 wherein the bibulous carrier is a nitrocellulose membrane wherein non-specific adsorption sites have been blocked to facilitate transport of the target molecules.

7. Apparatus according to claim 1 wherein the bibulous carrier is a glass fiber matrix.

8. Apparatus according to claim 1 wherein the disintegratable barrier is disintegrated by the liquid sample.

9. Apparatus according to claim 1 wherein the disintegratable barrier is disintegrated by a substance added to the liquid sample.

10. Apparatus according to claim 1 wherein the disintegratable barrier is disintegrated by a solution applied to the sample area after the liquid sample is applied.

11. Apparatus according to claim 1 wherein the disintegratable barrier is disintegrated by a substance applied to the reaction area after binding of the target molecules to the reaction area.

12. Apparatus according to claim 1 wherein the disintegratable barrier is disintegrated over a predetermined period of time.

13. Apparatus according to claim 1 wherein the disintegratable barrier is fabricated from a netting embedded in a compound selected from the group consisting of water soluble polymers, pH degradable substances, ionic strength degradable substances and enzymatically digestible substances.

14. Apparatus according to claim 13 wherein the water soluble polymers comprise water soluble polyesters.

15. Apparatus according to claim 1 wherein the target molecules comprise target nucleic acid sequences.

16. Apparatus according to claim 15 wherein the target nucleic acid sequences comprise DNA sequences.

17. Apparatus according to claim 15 wherein the target nucleic acid sequences comprise RNA sequences.

18. Apparatus according to claim 1 wherein the target molecules comprise antigens.

19. Apparatus according to claim 1 wherein the target molecules comprise antibodies.

20. Apparatus according to claim 15 wherein the capture reagent comprises at least one nucleic acid capture reagent including nucleic acid probe sequences complementary to at least part of the target nucleic acid sequences.

21. Apparatus according to claim 1 wherein the capture reagent comprises at least one antigen.

22. Apparatus according to claim 1 wherein the capture reagent comprises at least one antibody.

* * * * *

UNITED STATES PATENT AND TRADEMARK OFFICE
CERTIFICATE OF CORRECTION

PATENT NO. : 5,698,395
DATED : December 16, 1997
INVENTOR(S) : Menachem RITTERBAND et al.

It is certified that error appears in the above-identified patent and that said Letters Patent is hereby corrected as shown below:

On the title page: -add- Assignee: ORGENICS LTD., P.O.BOX 360, Yavne 60650, Israel.

Signed and Sealed this

Eighteenth Day of May, 1999

*Attest:*

Q. TODD DICKINSON

*Attesting Officer*     *Acting Commissioner of Patents and Trademarks*